United States Patent [19]

Tanaka et al.

[11] Patent Number: 4,701,210
[45] Date of Patent: Oct. 20, 1987

[54] N-SUBSTITUTED GLUTAMIC ACID DERIVATIVE AND PROCESS FOR PRODUCTION AND USE THEREOF

[75] Inventors: Takaharu Tanaka, Osaka; Naoki Higuchi, Ikeda; Masayuki Saito; Masaki Hashimoto, both of Ibaraki, all of Japan

[73] Assignee: Suntory Limited, Osaka, Japan

[21] Appl. No.: 875,079

[22] Filed: Jun. 17, 1986

[30] Foreign Application Priority Data

Jun. 18, 1985 [JP] Japan ................... 60-130811

[51] Int. Cl.$^4$ ............................. A01N 37/24
[52] U.S. Cl. ............................. 71/98; 71/114; 71/116; 562/444; 562/426; 562/431
[58] Field of Search ............ 562/444, 426, 431; 71/98, 114, 116

[56] References Cited

U.S. PATENT DOCUMENTS 2,453,983 11/1948 Archibald et al. ............ 71/116
3,364,249 1/1968 Bolhofer ...................... 562/431
4,116,677 9/1978 Walker et al. ................. 71/116
4,465,507 8/1984 Konno et al. .................. 71/98

FOREIGN PATENT DOCUMENTS 2948095 6/1981 Fed. Rep. of Germany ...... 562/444
1544786 11/1968 France ......................... 71/416
1223062 4/1969 United Kingdom ............. 562/443

OTHER PUBLICATIONS

Chkanikov et al., Chem. Abst., vol. 88, #165330n (1978).
El-Noggar et al. Indian J. Chem., vol. 20 B, pp. 484–486 (1981).

Primary Examiner—James H. Reamer
Attorney, Agent, or Firm—Burns, Doane, Swecker & Mathis

[57] ABSTRACT

N-substituted glutamic acid derivative and salt thereof, a process for production thereof comprising acylation of glutanic acid or derivative thereof, a herbicidal composition comprising the compound, and a method for killing or controlling plants using the compound. The compounds have a selective herbicidal effect.

8 Claims, No Drawings

N-SUBSTITUTED GLUTAMIC ACID DERIVATIVE AND PROCESS FOR PRODUCTION AND USE THEREOF

BACKGROUND OF THE INVENTION

1. Field of the Invention

The present invention relates to a novel N-substituted glutamic acid derivative, and a process for the production and use thereof. The derivative exhibits a strong herbicidal activity, and is useful as an active ingredient for various kinds of agricultural chemicals.

2. Description of the Related Art

A series of phenoxy compounds including 2,4-dichlorophenoxyacetic acid, 2-methyl-4-chlorophenoxyacetic acid, and the like have been used as herbicides important for agriculture and gardening. Novel, L., French Pat. No. 1,544,786, discloses p-halogenophenoxyacetic acid compounds. The biological actions of these phenoxy herbicides mainly rely on the destruction in vivo of the auxin balance, which provides a disturbance of the fundamental physiological actions in a plant, including abnormal cell division, abnormal morphology, inhibition of chlorophyll formation, and abnormal cell walls resulting in a rise of the osmotic pressure. Since the auxin hormone type herbicides can be applied to soil as well as the stem and leaves of a plant, and transported within a plant, such herbicides exhibit a herbicidal action on perennial weeds in, for example, a rice field, on which other types of herbicides have no herbicidal action. Moreover, the auxin hormone type herbicides strongly inhibit regeneration of the treated weeds.

Such phenoxy type herbicides, however, can provide undesirable side effects on important crops such as rice, wheat, barley, and the like, and are not effective on some perennial weeds, and therefore, are used only for limited applications and by limited methods.

SUMMARY OF THE INVENTION

Therefore, the present invention is directed to a novel phenoxy type herbicide which provides no or very little undesirable side effects on important crops including rice, wheat, barley and the like, exhibits a selective herbicidal effect on monocotyledons or broad-leaved plants and is stable when applied, maintaining the above-mentioned advantages of the phenoxy type herbicide.

More particularly, the present invention provides a compound having the formula (I), which compound exhibits a herbicidal effect.

The present invention also provides a process for the production of the compound having the formula (I).

The present invention also provides a herbicidal composition containing said compound as an active ingredient.

The present invention also provides a method for killing or controlling weeds.

DESCRIPTION OF THE PREFERRED EMBODIMENT

The present N-substituted glutamic acid derivative has the following general formula (I):

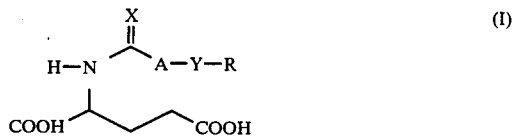

wherein X and Y represent, independently, an oxygen atom or a sulfur atom; a group —A— represents a methylene group, ethylene group, or ethylidene group; R represents a di-substituted phenyl group, naphthyl group, tolyl group, trifluoromethylphenyl group, iodophenyl group, fluorophenyl group, or chlorophenyl group; with the proviso that if both X and Y represent an oxygen atom and the group —A— represents a methylene group, R represents a group other than p-chlorophenyl group, p-iodophenyl and p-fluorophenyl.

Substituents in the di-substituted phenyl group as R include the dichlorophenyl group, dibromophenyl group, bromochlorophenyl group, dimethoxyphenyl group, chlorotolyl group, dimethylphenyl group, chlorotrifluoromethylphenyl group, chloromethoxyphenyl group, chlorofluorophenyl group and chloroiodophenyl group.

The above-mentioned N-substituted glutamic acid derivative (I) is produced, for example, by reacting glutamic acid represented by the following formula (II):

with an acid halide, an active ester compound or an acid anhydride represented by the following formula (IIIa) or (IIIb):

or

wherein R, Y and A have the same meanings as defined above, and R¹ represents a halogen atom, or forms, with CO, an active ester group, in the presence or absence of a base in water or an organic solvent, to obtain a compound of the present invention represented by the following formula (Ia):

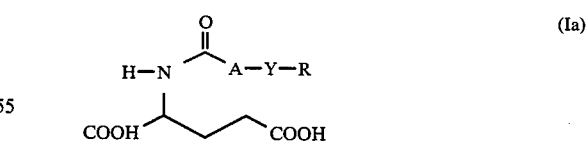

wherein A, Y and R have the same meanings as defined above.

The base used for the above-mentioned reaction is preferably an alkaline metal hydroxide such as sodium hydroxide, potassium hydroxide or lithium hydroxide, or a trialkylamine such as trimethylamine, triethylamine, dimethylethylamine, methyldiethylamine or the like.

The reactions are preferably carried out at a temperature lower than room temperature, preferably at 0° C. to 20° C., for 1 to 12 hours with stirring.

In the second embodiment, a diester of glutamic acid represented by the following formula (IIa):

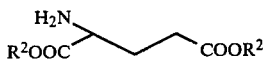
(IIa)

wherein $R^2$ represents a lower alkyl group, is reacted with the compound represented by the formula (IIIa) or (IIIb) described above under the presence or absence of a base in water or an organic solvent, in the same manner as described above for the first embodiment, to form an intermediate diester represented by the following formula (IV):

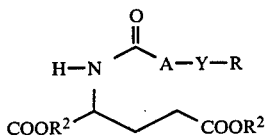
(IV)

wherein R, Y and A have the same meanings as described above. The resulting intermediate is hydrolysed to obtain a compound of the present invention of the formula (Ia). The hydrolysis is carried out according to a conventional method for hydrolysis of an ester bond, such as acid hydrolysis or alkaline hydrolysis.

In the third embodiment, the compound of the formula (IIa) is condensed with a carboxylic acid represented by the following formula (IIIc):

R—Y—A—COOH  (IIIc)

wherein R, Y and A have the same meanings as defined above, under the same condition as described for the first and second embodiments, or by using a conventional condensation agent used for peptide synthesis, such as 1-ethyl-3-(3-dimethylaminopropyl)carbodiimide, dicyclohexylcarbodiimide, or the like, to obtain an intermediate diester of the formula (IV), which intermediate is then hydrolysed to obtain a compound of the formula (Ia) in the same manner as described for the second embodiment.

For production of the formula (I) of the present invention wherein X represents a sulfur atom, a diester compound of the formula (IV) is treated with phosphorus pentaoxide in carbon disulfide to form an intermediate diester wherein X represents a sulfur atom, which ester is then hydrolysed to form a compound of the present invention represented by the following formula (Ib):

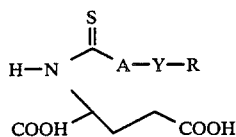
(Ib)

wherein A, Y and R have the same meanings as defined above. The starting material of the formula (IV) may be produced according to the second or third embodiment described above, or by esterifying a compound of the formula (Ia.) The esterification is carried out, for example, by treating a compound of the formula (Ia) with hydrogen chloride in ethanol or with thionyl chloride in ethanol. The hydrolysis of the intermediate is carried out, for example, by treating the intermediate diester with an alkaline metal hydroxide such as sodium hydroxide or potassium hydroxide in water or an aqueous medium.

Most preferably, an acid chloride of the following formula (IIId):

R—Y—A—COCl  (IIId)

wherein R, Y and A have the same meanings as defined above, is treated with glutamic acid in an aqueous solution of alkaline metal hydroxide to form a compound of the present invention represented by the formula (Ia).

The present compound thus synthesized is purified according to a conventional purification process, such as column chromatography, preparative thin-layer chromatography, and the like.

The present compound of the general formula (Ia) and (Ib) can be converted to corresponding salts thereof, such as sodium salt, potassium salt, lithium salt, and ammonium salt, by treating the compound (I) with sodium hydroxide, potassium hydroxide, lithium hydroxide, and aqueous ammonia respectively.

The compound of the present invention has a weak toxicity for humans and domestic animals, and exhibits a highly specific and strong growth-inhibiting effect on monocotyledons or broad-leaved plants. Therefore, the present compound may be widely used as an agricultural chemical.

When the compound of the present invention is used as a herbicide, it may be used by mixing with a solid carrier such as clay or diatomaceous earth, or with a liquid carrier, such as water, or alcohols such as ethanol, propanol or butanol, aromatic hydrocarbons such as benzene, toluene or xylene, ethers such as dimethoxyethan or dioxane, ketones such as methylethyl ketone, or esters such as ethyl acetate or butyl acetate. Alternatively, the present compound may be formulated into emulsions, suspensions, powders, wettable powders, glanules, concentrated emulsions, and the like. The formulations are prepared according to a conventional procedure such as dissolving, mixing, milling, granulating, and the like, using the above-mentioned carrier, if necessary by adding an emulsifying agent, suspending agent, dispersing agent, stabilizing agent, spreading agent or the like. The herbicidal formulations can contain, in addition to the present compound, another kind of herbicide, insecticide, plant-growth regulator, or the like. Usually, such formulations contain 0.5 to 90% by weight of the present compound.

The amount of the present compound used as a herbicide varies depending upon the kinds of weeds to be killed, kind of crop to be protected, etc., and is usually 20 g to 500 g per 10 acres.

EXAMPLES

The present invention will now be further illustrated by, but is by no means limited to, the following examples.

EXAMPLE 1

N-(2,4-dichlorophenoxy)acetyl-L-glutamic acid
(Compound SUAM 3604)

10 m moles of L-glutamic acid was dissolved in 20 ml of 1 N sodium hydroxide aqueous solution, and the resulting aqueous solution was diluted with water to 40 ml. To the aqueous solution, a solution of 10 m moles of 2,4-dichlorophenoxyacetyl chloride dissolved in 10 ml of benzene was slowly added dropwise with cooling and stirring. Immediately after, 10 ml of 1 N sodium hydroxide aqueous solution was added. The reaction mixture was then allowed to warm to a room temperature, and stirred at a room temperature for one day.

After the reaction was completed, the reaction mixture was extracted twice with ethyl ether to eliminate the unreacted 2,4-dichlorophenoxyacetyl chloride. The aqueous phase was acidified with hydrochloric acid to precipitate a product, which was then extracted three times with ethyl acetate, and the ethyl acetate phase was evaporated to eliminate solvent. The resulting residue was recrystallized from ethyl acetate/benzene/hexane to obtain a colorless crystal of the title compound.

According to the same procedure as described above, except that the following acid chloride was used in place of 2,4-dichlorophenoxyacetyl chloride, the following products were obtained: N-(o-chlorophenoxy)-acetyl-L-glutamic acid (Compound SUAM 3609) from o-chlorophenoxyacetyl chloride; N-(o-methylphenoxy)acetyl-L-glutamic acid (Compound SUAM 3610) from o-methoxyphenoxyacetyl chloride; N-(m-trifluoromethylphenoxy)-acetyl-L-glutamic acid (Compound SUAM 3611) from m-trifluoromethylphenoxyacetyl chloride; N-(m-chlorophenoxy)acetyl-L-glutamic acid (Compound SUAM 3612) from m-chlorophenoxyacetyl chloride; N-(p-methylphenoxy)-acetyl-L-glutamic acid (Compound SUAM 3614) from p-methylphenoxyacetyl chloride; and N-(4-chloro-2-methylphenoxy)acetyl-L-glutamic acid (Compound SUAM 3603) from 4-chloro-2-methylphenoxyacetyl chloride. All of the products were colorless crystals.

EXAMPLE 2

N-(p-chlorophenoxyethane)thioyl-L-glutamic acid (Compound SUAM 3602)

According to the same procedure as described in Example 1, except that 10 m moles of p-chlorophenoxyacetyl chloride was used in place of 2,4-dichlorophenoxyacethyl chloride, N-(p-chlorophenoxy)acetyl-L-glutamic acid was obtained.

12 m moles of N-(p-chlorophenoxy)acetyl-L-glutamic acid was added to a solution prepared by adding dropwise with cooling 30 m moles of thionyl chloride to 13 ml of absolute ethanol, and the resulting reaction mixture was stirred at a room temperature for one day. By distilling off thionyl chloride and ethanol, N-(p-chlorophenoxy)acetyl-L-glutamic acid α,γ-diethyl ester was obtained.

8 m moles of the ester was dissolved in 15 ml of chloroform, and the resulting solution was slowly added dropwise to a solution of 1.8 g of phosphorous pentaoxide dissolved in 3.5 ml of carbon disulfide. The reaction mixture was stirred at 55° C. to 60° C. for one day. The reaction mixture was then evaporated under a reduced pressure to eliminate solvents and obtain a crude product. The product was purified by silica gel chromatography, the purified product was dissolved in a mixture consisting of 20 ml of 1 N sodium hydroxide aqueous solution and 20 ml of methanol, and the resulting solution was stirred for one day. The reaction mixture was evaporated to eliminate methanol, and the residual aqueous phase was acidified with hydrochloric acid to form a precipitate, which was then extracted three times with ethyl acetate, and the extract was dried on anhydrous magnesium sulfate. The dried extract was evaporated, and the residue was recrystallized from ethyl ether to obtain the title compound as a crystal.

EXAMPLE 3

N-(β-naphtoxyacetyl)-L-glutamic acid (Compound SUAM 3608)

According to the same procedure as described in Example 1, except that β-naphtoxyacetyl chloride was used in place of 2,4-dichlorophenoxyacetyl chloride, the title compound was obtained as a colorless crystal.

Moreover, by using α-naphtoxyacetyl chloride in place of β-naphtoxyacetyl chloride, N-(α-naphtoxyacetyl)-L-glutamic acid (Compound SUAM 3617) was obtained as a colorless crystal.

EXAMPLE 4

N- α-(p-chlorophenoxy)propionyl -L-glutamic acid (Compound SUAM 3605)

40 m moles of p-chlorophenol and 40 m moles of DL-α-chloropropionic acid were dissolved in 15 ml of 5 N sodium hydroxide solution, and the mixture was evaporated to dryness with heating and stirring. The dried reaction mixture was dissolved in 100 ml of water, and the resulting solution was allowed to cool to a room temperature and acidified to about pH 2 with hydrochloric acid. The acidified aqueous solution was extracted with ethyl ether, and the ether phase was separated and dried on anhydrous magnesium sulfate. The ether was distilled off to obtain a residue. The residue was crystallized from benzene to obtain α-[(R,S)-p-chlorophenoxy]propionic acid. To 15 m moles of α-[(R,S)-p-chlorophenoxy]propionic acid 60 m moles of thionyl chloride was added, and the mixture was refluxed for three hours with heating. Excessive thionyl chloride was distilled off, and the residue was distilled under a reduced pressure to obtain α-[(R,S)-p-chlorophenoxy]propionyl chloride as a colorless oil. 10 m moles of α-[(R,S)-p-chlorophenoxy]propionyl chloride was treated in the same procedure as described in Example 1 to obtain the title compound as a crystal.

EXAMPLE 5

N-(p-chlorophenoxypropionyl)-L-glutamic acid (Compound SUAM 3606)

10 m moles of p-chlorophenoxypropionic acid was treated with 40 m moles of thionyl chloride for 30 minutes with heating to obtain p-chlorophenoxypropionyl chloride. The 10 m moles of p-chlorophenoxypropionyl chloride thus obtained was treated in the same procedure described in Example 1 to obtain the title compound as a colorless crystal.

EXAMPLE 6

N-(p-chlorophenylthio)acetyl-L-glutamic and (Compound SUAM 3607)

The same procedure as described in Example 4 was carried out, except that using 40 m moles of p-chlorophenylthiol in place of p-chlorophenol, p-chlorophenylthioacetic acid was synthesized. Next, the same procedure as described in Example 4 was carried out, except that using p-chlorophenylthioacetic acid in place of α-[(R,S)-p-chlorophenoxy]propionic acid, p-chlorophenylthioacetyl chloride was synthesized.

p-chlorophenylthioacetyl chloride was then treated according to the same procedure as described in Example 1 to obtain the title compound as a colorless crystal.

The properties of the compounds prepared in Examples 1 to 6 are set forth in Table 1.

TABLE 1

Structure:
HN-Z
|
COOH—L—COOH

| (Exp. No.) SUAM-No. | Substituent Z = | Appearance Melting point (°C.) | IR-Spectrum (KBr, cm⁻¹) | NMR-Spectrum (CD₃OD, w ppm, J is shown by Hz) | Mass spectrum (M/Z) | Elemental analysis |
|---|---|---|---|---|---|---|
| (1) 3604 | Z = —C(=O)—CH₂—O—(2,4-dichlorophenyl) | Colorless crystal 126–130 | 3370, 1720 1630, 1470 1230, 790 | 2.16 (2H, m), 2.35 (2H, m) 4.56 (1H, m), 4.64 (2H, s) 7.04 (1H, d, J = 8.8), 7.25 (1H, dd, J = 8.8, 2.8), 7.44 (1H, d, J = 2.8) | 350 (M⁺) | — |
| (1) 3609 | Z = —C(=O)—CH₂—O—(2-chlorophenyl) | Colorless crystal 167–168 | 3380, 1725 1630, 1540 1480, 1220 750 | 2.16 (2H, m), 2.34 (2H, m) 4.56 (1H, m), 4.64 (2H, s) 7.02 (2H, m), 7.34 (2H, m) | — | Calc. C (%) 49.46 H (%) 4.47 N (%) 4.44<br>Found 49.68 4.36 4.73<br>(C₁₃H₁₄NO₆Cl) |
| (1) 3610 | Z = —C(=O)—CH₂—O—(2-methylphenyl) | Colorless crystal 158–159 | 3400, 1730 1635, 1540 1500, 1255 1220, 760 | 2.12 (2H, m), 2.34 (2H, m) 4.57 (1H, m), 4.57 (2H, s) 2.32 (3H, s), 7.00 (4H, m) | 295 (M⁺) | Calc. C (%) 56.95 H (%) 5.80 N (%) 4.74<br>Found 56.88 5.82 4.75<br>(C₁₄H₁₇NO₆) |
| (1) 3611 | Z = —C(=O)—CH₂—O—(3-trifluoromethylphenyl) | Colorless crystal 159–160 | 3390, 1730 1720, 1620 1330, 1185 1130, 790 | 2.15 (2H, m), 2.34 (2H, m) 4.54 (1H, m), 4.64 (2H, s) 7.37 (4H, m) | 349 (M⁺) | Calc. C (%) 48.15 H (%) 4.04 N (%) 4.01<br>Found 48.29 4.00 4.14<br>(C₁₄H₁₄NO₆F₃) |
| (1) 3612 | Z = —C(=O)—CH₂—O—(3-chlorophenyl) | Colorless crystal 151–152 | 3380, 1730 1710, 1620 1595, 1550 1240, 1190 1155, 775 | 2.14 (2H, m), 2.33 (2H, m) 4.57 (1H, m), 4.50 (2H, s) 6.97 (3H, m), 7.26 (1H, t, J = 8.0) | 315 (M⁺) | Calc. C (%) 49.46 H (%) 4.47 N (%) 4.44<br>Found 49.55 4.34 4.58<br>(C₁₃H₁₄NO₆Cl) |
| (1) 3614 | Z = —C(=O)—CH₂—O—(4-methylphenyl) | Colorless crystal 124–126 | 3380, 1720 1620, 1540 1500, 1235 1220, 810 | 2.12 (2H, m), 2.25 (3H, s), 2.34 (2H, t, J = 7.2), 4.53 (1H, dd, J = 4.8, 9.6), 4.51 (2H, s), 6.88 (2H, d, J = 8.9), 7.08 (2H, d, J = 8.9) | — | Calc. C (%) 56.95 H (%) 5.80 N (%) 4.74<br>Found 57.39 5.73 4.69<br>(C₁₄H₁₇NO₆) |

TABLE 1-continued structure: HN-Z / L / COOH, COOH

| (Exp. No.) SUAM-No. | Substituent | Appearance Melting point (°C.) | IR-Spectrum (KBr, cm⁻¹) | NMR-Spectrum (CD₃OD, w ppm, J is shown by Hz) | Mass spectrum (M/Z) | Elemental analysis |
|---|---|---|---|---|---|---|
| (1) 3603 | Z = −C(=O)−CH₂−O−(2-CH₃, 4-Cl phenyl) | Colorless crystal 162–163 | 3380, 1720 1630, 1490 1245, 1190 800 | 2.10 (2H, m), 2.32 (2H, m) 4.52 (1H, m), 4.56 (2H, s) 2.28 (3H, s), 6.82 (1H, dd, J = 2.0, 7.2), 7.10 (1H, dd, J = 3.2, 7.2), 7.16 (1H, dd, J = 3.2, 2.0) | 329 (M⁺) | Calc. C 51.00 H 4.89 N 4.25<br>Found 51.13 4.80 4.38 (C₁₄H₁₆NO₆Cl) |
| (2) 3602 | Z = −C(=S)−CH₂−O−(4-Cl phenyl) | Colorless crystal 144–145 | 3445, 1720 1670, 1530 1480, 1270 820 | 2.32 (4H, m), 4.90 (2H, s) 5.15 (1H, m), 6.98 (2H, d, J = 9.1), 7.25 (2H, d, J = 9.1) | — | Calc. C 47.06 H 4.25 N 4.22<br>Found 46.35 4.21 4.36 (C₁₃H₁₄NO₅SCl) |
| (3) 3608 | Z = −C(=O)−CH₂−O−(2-naphthyl) | Colorless crystal 162.5–163.5 | 3390, 1730 1625, 1530 1480, 1270 1185, 840 | 2.10 (2H, m), 2.35 (2H, m) 4.60 (1H, m), 4.68 (2H, s) 7.30 (4H, m), 7.75 (3H, m) | 331 (M⁺) | Calc. C 61.63 H 5.17 N 4.23<br>Found 61.68 5.13 4.28 (C₁₇H₁₇NO₆) |
| (3) 3617 | Z = −C(=O)−CH₂−O−(1-naphthyl) | Colorless crystal 180–182 | 3415, 1720 1645, 1270 1240, 1195 795, 770 | 2.10 (2H, m), 2.32 (2H, m) 4.60 (1H, m), 4.72 (2H, s) 6.85 (1H, m), 7.40 (3H, m) 7.76 (1H, m), 8.32 (1H, m) | 331 (M⁺) | Calc. C 61.63 H 5.17 N 4.23<br>Found 61.47 5.18 4.25 (C₁₇H₁₇NO₆) |
| (4) 3605 | Z = −C(=O)−CH(CH₃)−O−(4-Cl phenyl) | Colorless crystal 144–145 | 3270, 1710 1650, 1530 1485, 1280 1235, 835 | 0.96 (3H, d, J = 9.2), 1.70 (2H, m), 1.98 (2H, m), 4.82 (1H, m), 4.16 (1H, d, J = 9.2), 7.13 (2H, d, J = 12.0), 7.56 (2H, d, J = 12.0) | 329 (M⁺) | Calc. C 51.00 H 4.89 N 4.25<br>Found 51.04 4.81 4.29 (C₁₄H₁₆NO₆Cl) |
| (5) 3606 | Z = −C(=O)−CH₂CH₂−O−(4-Cl phenyl) | Colorless crystal 123.5–124.5 | 3390, 1735 1690, 1640 1490, 1235 825 | 2.10 (2H, m), 2.40 (2H, m), 2.69 (2H, t, J = 6.8), 3.21 (2H, t, J = 6.8), 4.47 (1H, dd, J = 4.2, 8.4), 6.88 (2H, d, J = 9.1), 7.20 (2H, d, J = 9.1) | — | Calc. C 51.00 H 4.89 N 4.25<br>Found 51.16 4.84 4.42 (C₁₄H₁₆NO₆Cl) |

TABLE 1-continued

Structure: HN-Z / L / COOH ... COOH

| (Exp. No.) SUAM-No. | Substituent | Appearance Melting point (°C.) | IR-Spectrum (KBr, cm⁻¹) | NMR-Spectrum (CD₃OD, w ppm, J is shown by Hz) | Mass spectrum (M/Z) | Elemental analysis |
|---|---|---|---|---|---|---|
| (6) 3607 | Z=−C(=O)−CH₂−S−C₆H₄−Cl (4-Cl) | Colorless crystal 152–153 | 3280, 1710 1640, 1520 1480, 1280 815 | 2.00 (2H, m), 2.22 (2H, m) 3.66 (2H, s), 4.42 (1H, dd, J = 4.8, 8.8), 7.34 (4H, dd, J = 4.8, 8.8) | 331 (M⁺) | Calc. C(%) 47.06 H(%) 4.25 N(%) 4.22<br>Found 47.18 4.24 4.25<br>(C₁₃H₁₄NO₅SCl) |

EXAMPLE 7

The compounds of the present invention were evaluated for their selective herbicidal activity on broad-leaved plants, i.e., cucumber and radish, and monocatylenodons, i.e., rice, wheat, and barnyard grass.

The test was carried out as a before-germination test and an after-germination test.

For the before-germination test for cucumber and radish, five each of seeds of these plants were seeded in soil contained in a pot 6×15×15 cm in size. Immediately after the seeding, 60 ml per part of aqueous acetone solution containing a predetermined amount of test compound was applied to the pot. The aqueous solution of the test compound was prepared so that the above-mentioned application provides 200 g or 50 g of the test compound per 10 acres. For the after-germination test, for cucumber and radish, the seeds thereof were germinated and grown in a greenhouse until each plant had two to three leaves, and the two lots of seedlings were transplanted to a pot as described for the before-germination test, and immediately after the transplanting, the test compound was applied as described above.

For the before-germination test for rice, barley and barnyard grass, ten each of seeds of these plant were seeded at a depth of 1 to 2 cm in soil from a rice field contained in a pot 20×10×6 cm in size, submerged to a depth of about 3 cm, and 60 ml of an aqueous solution of test compound was incorporated in the water in the pot. The aqueous solution was prepared so that the above-mentioned application provides 200 g or 50 g of the test compound per 10 acres. For the after-germination test for rice, barley and barnyard grass, the seeds thereof were germinated and grown in a greenhouse until each plant had 2 to 3 leaves, and the two lots of seedlings were transplanted to a pot as described for the before-germination test, and immediately after the transplanting, the test compound was applied as described above.

After the application of the test compounds, the growth of the plants was observed, and the herbicidal effect evaluated by scores of 5 (complete killing) to 0 (not effective).

The results are set forth in Tables 2 and 3.

TABLE 2

| Test compound (Exp. No.) SUAM No. | Amount of application (g/10 ares) | Before-germination test | | | | |
|---|---|---|---|---|---|---|
| | | Broad-leaved plant | | Monocotylenodons | | |
| | | Cu-cumber | Rad-ish | Rice | Wheat | Barn-yard grass |
| (1) | 200 | 5 | 5 | 5 | 5 | 5 |
| 3604 | 50 | 4 | 4 | 4 | 4 | 4 |
| (1) | 200 | 4 | 3 | 0 | 0 | 0 |
| 3609 | 50 | 1 | 0 | 0 | 0 | 0 |
| (1) | 200 | 3 | 4 | 0 | 0 | 2 |
| 3610 | 50 | 2 | 3 | 0 | 0 | 1 |
| (1) | 200 | 4 | 4 | 0 | 4 | 4 |
| 3611 | 50 | 3 | 4 | 0 | 3 | 3 |
| (1) | 200 | 5 | 4 | 4 | 2 | — |
| 3612 | 50 | 3 | 4 | 1 | 0 | — |
| (1) | 200 | 2 | 4 | 0 | 0 | 0 |
| 3614 | 50 | 0 | 2 | 0 | 0 | 0 |
| (1) | 200 | 5 | 5 | 5 | 5 | 5 |
| 3603 | 50 | 4 | 4 | 4 | 4 | 4 |
| (2) | 200 | 5 | 5 | 3 | 4 | 4 |
| 3602 | 50 | 4 | 4 | 2 | 2 | 3 |
| (3) | 200 | 5 | 5 | 0 | 0 | 4 |
| 3608 | 50 | 4 | 4 | 0 | 0 | 3 |
| (4) | 200 | 5 | 4 | 2 | 3 | 4 |
| 3605 | 50 | 4 | 4 | 0 | 0 | 2 |
| (5) | 200 | 3 | 5 | 0 | 2 | 3 |
| 3606 | 50 | 1 | 4 | 0 | 0 | 2 |
| (6) | 200 | 5 | 0 | 2 | 2 | 3 |
| 3607 | 50 | 2 | 0 | 0 | 0 | 0 |

TABLE 3

| Test compound (Exp. No.) SUAM No. | Amount of application (g/10 ares) | After-germination test | | | | |
|---|---|---|---|---|---|---|
| | | Broad-leaved plant | | Monocotylenodons | | |
| | | Cu-cumber | Rad-ish | Rice | Wheat | Barn-yard grass |
| (3) | 200 | 4 | 4 | 0 | 0 | 3 |
| 3608 | 50 | 4 | 4 | 0 | 0 | 2 |

As seen from Tables 2 and 3, the compounds of the present invention exhibit a notable herbicidal effect.

In particular, the compounds SUAMs 3611, 3612, 3608, 3605, 3610 and 3606 exhibit selective herbicidal effects.

EXAMPLE 8

Typical herbicidal compositions of the present invention were prepared as follows.

| Granule | |
|---|---|
| Ingredient | Amount (part by weight) |
| The present compound | 5.5 |
| Benitoite | 54.5 |
| Talc | 40.0 |

The above-mentioned ingredients were mixed homogeneously and milled. The mixture was added with a small amount of water and mixed to form a paste. The paste was then granulated and dried.

| Emulsion | |
|---|---|
| Ingredient | Amount (part by weight) |
| The present compound | 20 |
| Tween-80 | 5 |
| Span-80 | 5 |
| Solvent naphtha | 70 |

The above-mentioned ingredients were mixed to form an emulsion.

| Wettable powder | |
|---|---|
| Ingredient | Amount (part by weight) |
| The present compound | 50 |
| Diatomaceous earth | 30 |
| Clay | 10 |
| Sodium raulyl sulfate | 10 |

The above-mentioned ingredients were mixed homogeneously.

We claim:

1. An N-substituted glutamic acid having the following general formula (I):

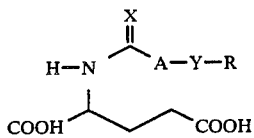 (I)

wherein X and Y represent, independently, an oxygen atom or a sulfur atom; a group —A— represents a methylene group, ethylene group, or ethylidene group; R represents a chlorotolyl group, dimethylphenyl group, chlorotrifluoromethylphenyl group, chloromethyloxyphenyl group, naphthyl group, tolyl group, trifluoromethyl phenyl group, iodophenyl group, fluorophenyl group, or chlorophenyl group; with a proviso that if both X and Y represent an oxygen atom and the group —A— represents a methylene group, R represents a group other than a p-chlorophenyl group, p-iodophenyl and p-fluorophenyl, and the sodium, potassium, lithium and ammonium salts thereof.

2. An N-substituted glutamic acid according to claim 1 wherein the compound is an optically active compound.

3. A herbicidal composition comprising an effective amount of an N-substituted glutamic acid derivative of claim 1 or the sodium, potassium, lithium or ammonium salts thereof, and a conventional carrier for herbicide.

4. A herbicidal composition according to claim 3 wherein the effective amount is 0.5 to 90% by weight.

5. A method for killing or controlling plants comprising applying an effective amount of an N-acyl amino acid derivative of claim 1 or salt thereof to a medium in which plants are to be killed or controlled.

6. A method according to claim 5 wherein the effective amount is 20 to 500 g per 10 acres.

7. A method for killing or controlling plants comprising applying an effective amount of a herbicidal composition of claim 3 to a medium in which plants are to be killed or controlled.

8. A method according to claim 7 wherein the effective amount is 20 to 500 g per acre.

* * * * *